US010744220B2

(12) United States Patent
Huang et al.

(10) Patent No.: US 10,744,220 B2
(45) Date of Patent: Aug. 18, 2020

(54) APPARATUS FOR EFFICIENT REMOVAL OF AIR POLLUTANTS

(71) Applicant: Honeywell International Inc., Morris Plains, NJ (US)

(72) Inventors: Kai Huang, Shanghai (CN); Marilyn Wang, Shanghai (CN); Xingping Wang, Shanghai (CN); Wesley Nie, Shanghai (CN); Hailin Liu, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 178 days.

(21) Appl. No.: 15/811,314

(22) Filed: Nov. 13, 2017

(65) Prior Publication Data

US 2019/0142988 A1    May 16, 2019

(51) Int. Cl.
| | | |
|---|---|---|
| *A61L 9/014* | (2006.01) | |
| *A61L 9/012* | (2006.01) | |
| *B01D 53/72* | (2006.01) | |
| *B01D 53/82* | (2006.01) | |
| *B01D 53/04* | (2006.01) | |

(52) U.S. Cl.
CPC .............. *A61L 9/014* (2013.01); *A61L 9/012* (2013.01); *B01D 53/0415* (2013.01); *B01D 53/72* (2013.01); *B01D 53/82* (2013.01); *A61L 2209/133* (2013.01); *A61L 2209/22* (2013.01); *B01D 2251/304* (2013.01); *B01D 2251/306* (2013.01); *B01D 2251/70* (2013.01); *B01D 2251/90* (2013.01); *B01D 2253/102* (2013.01); *B01D 2253/106* (2013.01); *B01D 2253/108* (2013.01); *B01D 2253/202* (2013.01); *B01D 2257/708* (2013.01)

(58) Field of Classification Search
CPC .... A61L 9/014; A61L 9/012; A61L 2209/133; A61L 2209/22; B01D 53/0415; B01D 53/82; B01D 53/72
See application file for complete search history.

(56) References Cited

U.S. PATENT DOCUMENTS

| | | | | |
|---|---|---|---|---|
| 6,010,562 A | * | 1/2000 | Flynn | ................. B01D 53/0415 96/125 |
| 7,014,682 B2 | * | 3/2006 | Hickerson | .......... B01D 53/0415 55/315.1 |
| 8,603,397 B2 | * | 12/2013 | Gruenbacher | ...... A01M 1/2033 422/124 |
| 10,226,546 B2 | * | 3/2019 | Leonaggeo | ........ B01D 53/0407 |
| 2004/0151617 A1 | * | 8/2004 | Zanakis | .................. A61L 9/145 422/4 |
| 2005/0214245 A1 | * | 9/2005 | Kim | ........................ A61L 9/014 424/76.1 |
| 2006/0000352 A1 | * | 1/2006 | Tower | .................... B01D 53/04 95/8 |
| 2008/0156194 A1 | * | 7/2008 | Withiam | ................ B01D 53/02 96/154 |

* cited by examiner

*Primary Examiner* — Regina M Yoo
(74) *Attorney, Agent, or Firm* — Schwegman Lundberg & Woessner, P.A.

(57) ABSTRACT

An apparatus for removing air pollutants from the air is described. The apparatus contains a fan module and a chamber that can hold either activated carbon or a gel that reacts with air pollutants from air.

20 Claims, 5 Drawing Sheets

APPARATUS FOR EFFICIENT REMOVAL OF AIR POLLUTANTS

BACKGROUND

Rapid economic development in many countries has resulted in increased environmental pollution. In particular, indoor environmental pollution caused by the use of various chemicals associated with the production of items such as decorative materials, furniture, tobacco, and household appliances is of growing concern. Many of the appliances, furnishings, and painted surfaces found in new home constructions release volatile organic compounds (VOCs). VOCs include hydrocarbons, carbonyl compounds, organic acids, organic peroxides, organic sulfur compounds, organic halides, and the like. VOCs can also participate in photochemical reaction with nitrogen oxides and sulfides of the atmosphere upon exposure to light and form highly toxic photochemical smog.

Many VOCs have been found to be carcinogenic or suspected carcinogens (such as formaldehyde, benzene, tetrachloroethylene, trichloroethane, trichlorethylene, and the like). Major emission sources of indoor air VOCs include wall coatings (e.g., paint and wallpaper) and oil paints and varnishes for furniture. However, recently, houses have become more and more airtight and, accordingly. VOCs can result in more serious health issues because they cannot rapidly escape the indoor environment.

There are a variety of commercial air fresheners and deodorizers that can temporarily mask the odor of some VOCs, but they do not fundamentally eliminate harmful sources of pollution, and can themselves act as new secondary pollution sources. Of the many VOC pollutants, there is widespread concern regarding the effective control of formaldehyde in paints and adhesives. Some commercially available products for formaldehyde removal are available; however, there is no effective product for removal of VOCs in general. Most commercially available products must be replaced when saturated, since there is no way for the consumer to change the adsorptive material therein.

SUMMARY OF THE INVENTION

In various embodiments, an apparatus for removing one or more air pollutants from air includes at least one fan unit; and a chamber containing activated carbon or a gel that removes one or more air pollutants.

Advantageously, the apparatus includes a cartridge that can be removed and replaced, which allows the consumer to simply replace the cartridge as needed without purchasing a new device. In various embodiments, the cartridges can contain activated carbon or gel for removing air pollutants from the air.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments of the present invention.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X. Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Apparatus for Removing Air Pollutants

In various embodiments, an apparatus for removing one or more air pollutants from air includes at least one fan unit. The apparatus also includes a chamber containing activated carbon or a gel that removes one or more air pollutants. Various embodiments include a chamber containing a gel that removes one or more air pollutants. In various embodiments, the fan unit comprises a battery. The battery can be any suitable battery or rechargeable battery, such as lithium batteries or nickel cadmium batteries. In various embodiments, the apparatus can also include circuitry to operate using an AC adapter that can plug into an electrical outlet. In some embodiments, the AC adapter can also recharge a rechargeable battery in the fan unit or in another portion of the apparatus.

Various embodiments include a chamber that includes a removable cartridge that includes activated carbon or gel for removing air pollutants. The chamber containing the activated carbon or gel that removes one or more air pollutants can be configured to accept a removable and replaceable module or cartridge containing the activated carbon or gel that removes one or more air pollutants. The user of the apparatus can, in various embodiments, remove a cartridge containing activated carbon and insert a cartridge that contains the gel that removes one or more air pollutants or a cartridge containing activated carbon, or vice versa. In this way, when the pollutant-removal capacity of the module or cartridge is diminished, the user can replace the cartridge or module with a new cartridge. In various embodiments, the cartridge or module contains all of the activated carbon or gel for removing air pollutants, such that when the cartridge is removed from the chamber there is substantially no activated carbon or gel in the chamber itself.

In various embodiments, the removable and replaceable cartridge includes only the gel, only the activated carbon, or a combination of activated carbon and gel. When the activated carbon and gel are present together, they may be arranged in any suitable manner in the cartridge that does not interfere with the operation and ability of the apparatus to remove air pollutants such as VOCs from the air. For example, the cartridge can include one or more layers of activated carbon (C), and one or more layers of gel (G), such that the ordering of the layers in the cartridge can be C-G-C, G-C-G, C-G-C-G, C-G-C-G-C, and the like. Each of the layers can be independently from 0.01 cm to 10 cm thick. A cartridge with both activated carbon and gel can also include optional binders or adhesives to keep the C and G layers together.

In various embodiments, the apparatus or fan unit includes an air inlet. When the fan is in operation, air enters the apparatus through the air inlet. The air inlet operably channels air into the chamber containing activated carbon and/or the gel. The apparatus or fan can further include an air outlet. Air that has had pollutants removed from it by the activated carbon and/or the gel can exit the apparatus through the air outlet. In various embodiments, the air passes from the chamber into the air outlet and out into the surrounding air.

In various embodiments, the concentration of one or more air pollutants exiting the air outlet is at least two times lower than the concentration of air pollutants entering the air inlet. The air pollutants can be any of the VOCs as described herein. In various embodiments, the apparatus reduces the concentration of one or more air pollutants outside of the apparatus to 0.1 to 1.0 ppm, 0.1 to 0.8 ppm, 0.1 to 0.6 ppm, 0.1 to 0.4 ppm, or 0.1 to 0.2 ppm, or any range or sub-range between these values. In various embodiments, the apparatus reduces the concentration of the one or more air pollutants to below 1 ppm, 0.9 ppm, 0.8 ppm, 0.7 ppm, 0.6 ppm, 0.5 ppm, 0.4 ppm, 0.3 ppm, 0.2 ppm, 0.1 ppm, or any range or sub-range between these values.

In various embodiments, the apparatus reduces the concentration of formaldehyde outside of the apparatus to 0.1 to 1.0 ppm, 0.1 to 0.8 ppm, 0.1 to 0.6 ppm, 0.1 to 0.4 ppm, or 0.1 to 0.2 ppm, or any range or sub-range between these values. In various embodiments, the apparatus reduces the concentration of formaldehyde to below 1 ppm, 0.9 ppm, 0.8 ppm, 0.7 ppm, 0.6 ppm, 0.5 ppm, 0.4 ppm, 0.3 ppm, 0.2 ppm, 0.1 ppm, or any range or sub-range between these values.

In various embodiments, the activated carbon can be 5 to 90 wt %, 5 to 85 wt %, 5 to 70 wt %, 5 to 65 wt %, 5 to 60 wt %, 5 to 55 wt %, 5 to 50 wt %, 5 to 45 wt %, 5 to 40 wt %, 5 to 35 wt %, 5 to 30 wt %, 5 to 25 wt %, 5 to 20 wt %, 5 to 15 wt %, 5 to 10 wt % of the apparatus, or any range or sub-range between these values. The activated carbon can be about 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, 5 wt % of the apparatus, or any range or sub-range between these values.

In various embodiments, the gel can be 5 to 90 wt %, 5 to 85 wt %, 5 to 70 wt %, 5 to 65 wt %, 5 to 60 wt %, 5 to 55 wt %, 5 to 50 wt %, 5 to 45 wt %, 5 to 40 wt %, 5 to 35 wt %, 5 to 30 wt %, 5 to 25 wt %, 5 to 20 wt %, 5 to 15 wt %, 5 to 10 wt % of the apparatus, or any range or sub-range between these values. The gel can be about 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, 5 wt % of the apparatus, or any range or sub-range between these values.

Figure 1:
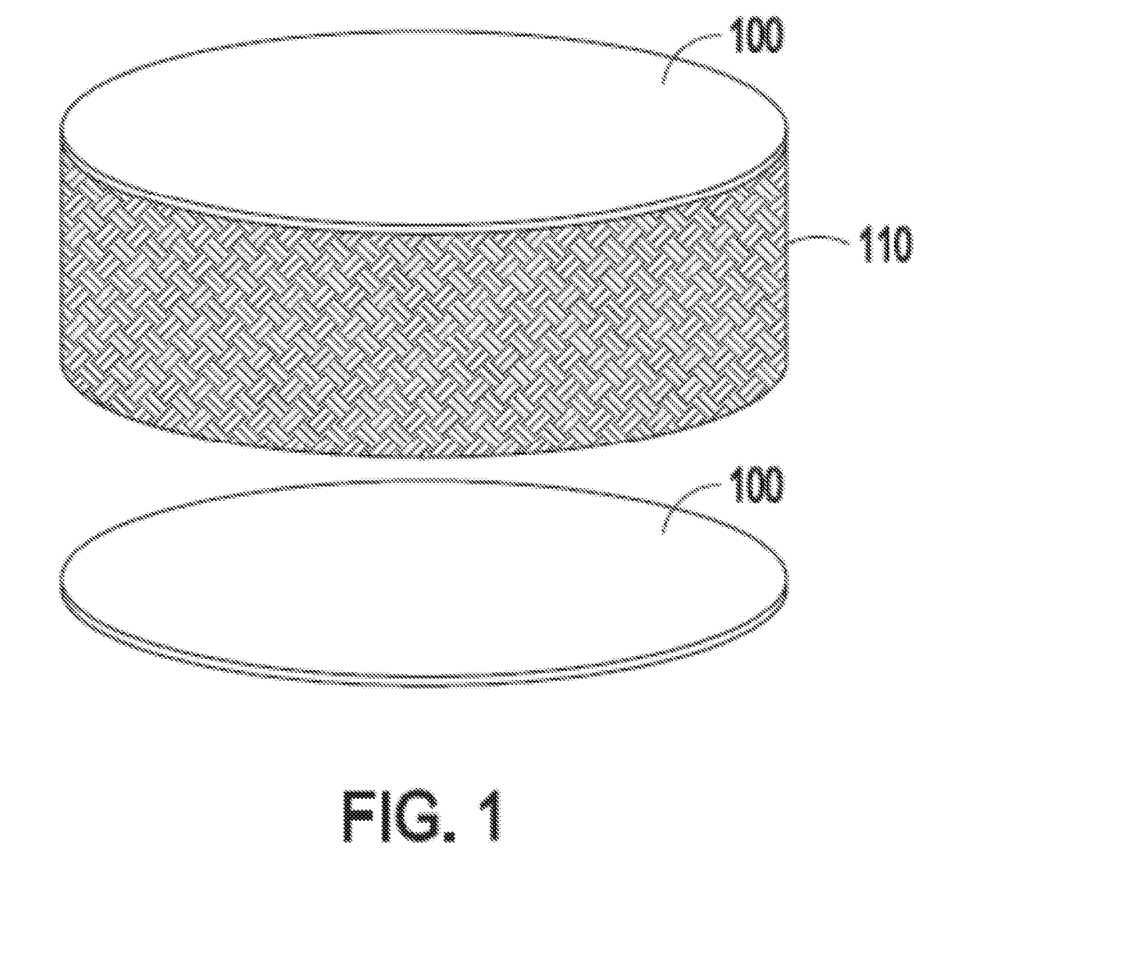
FIG. 1 is diagram of cartridge or module used in an apparatus for removing air pollutants, in accordance with various embodiments.
Figure 2:
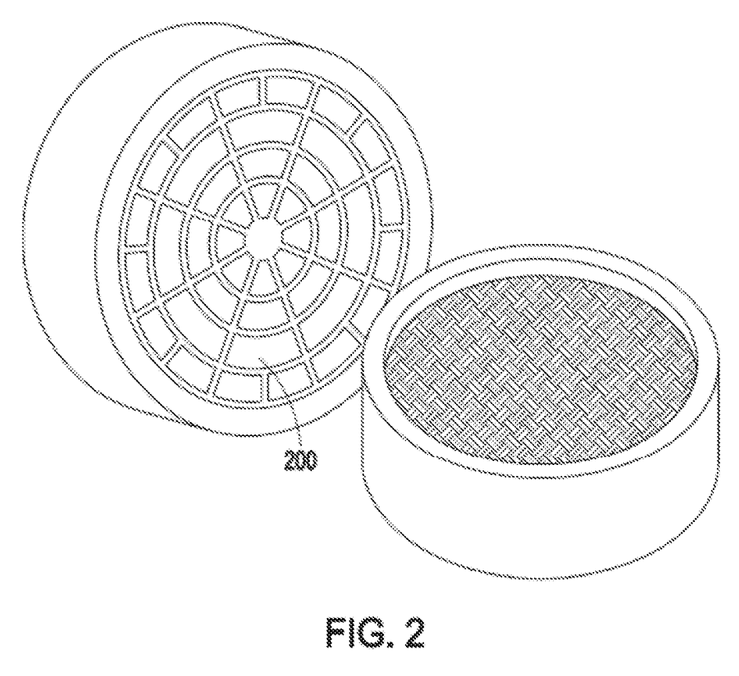
FIG. 2 is an air outlet in an apparatus for removing air pollutants, in accordance with various embodiments.
Figure 3:
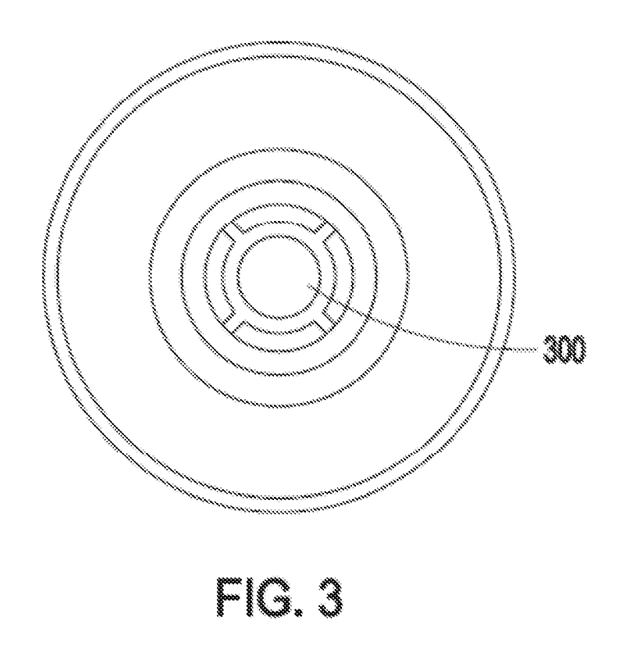
FIG. 3 is an air inlet in an apparatus for removing air pollutants, in accordance with various embodiments.

FIG. 1 shows a diagram of a cartridge or module used in an apparatus for removing air pollutants, in accordance with various embodiments. The cartridge or module contains a filter screen (100) and either activated carbon or gel (110). FIGS. 2 and 3 show an air outlet (200) and an air inlet (300), respectively, in an apparatus for removing air pollutants.

Figure 4:
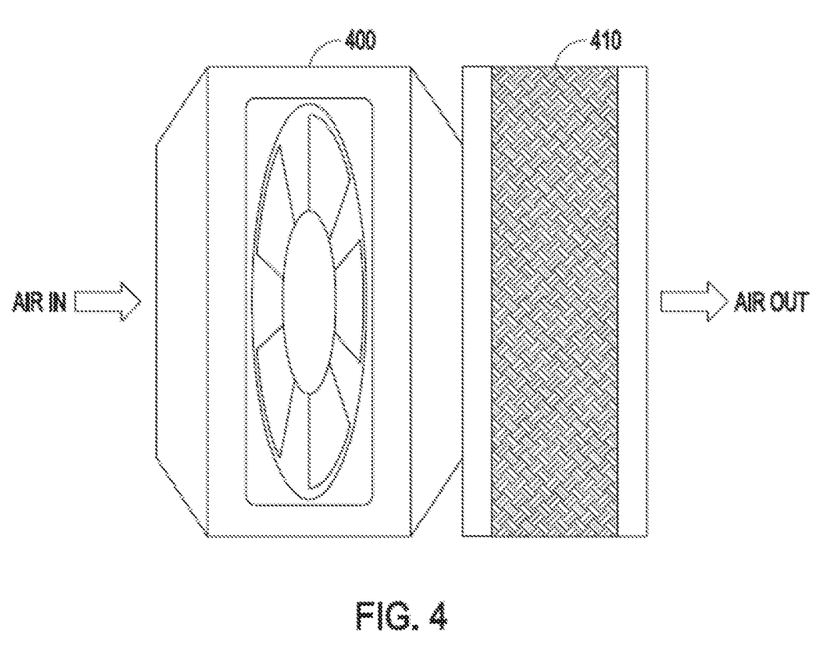
FIG. 4 is a schematic diagram of a fan module pushing air into a cartridge or module containing either activated carbon or gel, in accordance with various embodiments.
Figure 5:
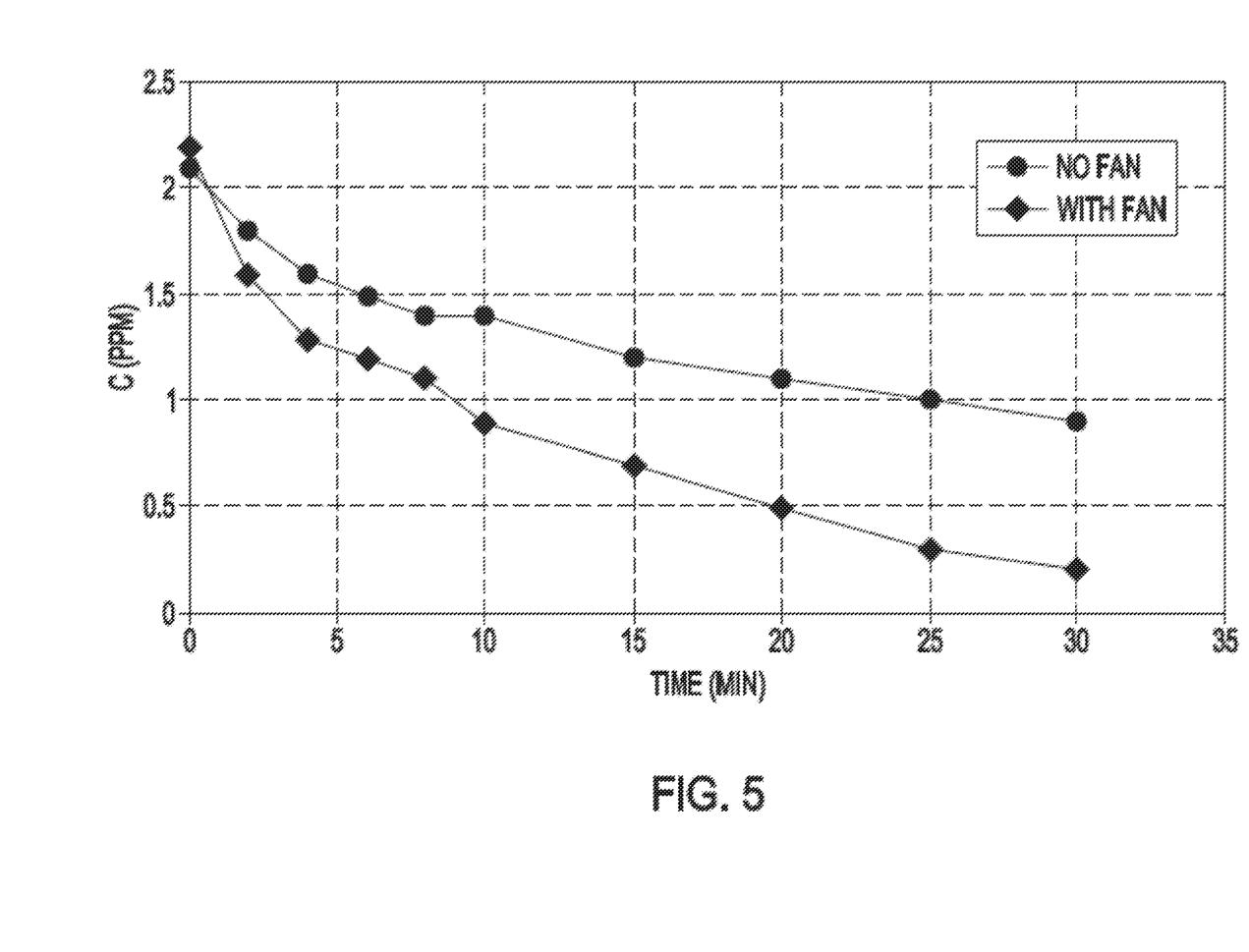
FIG. 5 is a chart comparing formaldehyde adsorption using an apparatus for removing air pollutants with a fan module and an apparatus with no fan, in accordance with various embodiments.

FIG. 4 is a schematic diagram of a fan module (400) pushing air into a cartridge or module containing either activated carbon or gel (410), in accordance with various embodiments. FIG. 5 is a chart comparing removal rates of formaldehyde using an apparatus for removing air pollutants with a fan module (fan on) and an apparatus with no fan, and using the gel formulation in Example 1. As seen in FIG. 5, formaldehyde is adsorbed at a higher rate when the fan in the fan module is on than when there is no fan used.

Gels for Removing Air Pollutants

In various embodiments, a gel for removing one or more air pollutants from air, includes at least one polymer, at least one adsorbent, at least one chelating agent, at least one component capable reactive with at least one air pollutant, and water.

The gel can be a hydrogel. The water content of the hydrogel can be about, 1 to 95 wt %, 1 to 90 wt %, 1 to 85 wt %, 1 to 80 wt %, 1 to 75 wt %, 1 to 70 wt %, 1 to 65 wt %, 1 to 60 wt %, 1 to 55 wt %, 1 to 50 wt %, 1 to 45 wt %, 1 to 40 wt %, 1 to 35 wt %, 1 to 30 wt %, 1 to 25 wt %, 1 to 20 wt %, 1 to 15 wt %, 1 to 10 wt %, 1 to 5 wt %, or any range or sub-range between these values. The water content of the hydrogel can be about 95 wt %, 90 wt %, 85 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, 9 wt %, 7 wt %, 6 wt %, 5 wt %, 4, wt %, 3 wt %, 2 wt %, 1 wt %, or any range or sub-range between these values. Various embodiments of the gel have a water content of about 80 to about 92 wt %. The hydrogel can also be subjected to freeze-drying or drying with supercritical fluid such as $CO_2$. In some embodiments, the hydrogel is freeze-dried and has a water content of about 1 to about 15 wt %.

In various embodiments, the at least one polymer is chosen from acacia, gelatin, carrageenan, locust bean gum, konjac gum, xanthan gum starch, cyclodextrin, sodium alginate, chitosan, carboxymethyl chitosan, polyvinyl alcohol, polyurea, and mixtures thereof. In various embodiments, the at least one polymer is carrageenan.

In various embodiments, the at least one polymer is about 1 to about 30 wt % of the gel. The at least one polymer can be about 1 to 25 wt %, 1 to 20 wt %, 1 to 15 wt %, 1 to 10 wt %, 1 to 9 wt %, 1 to 8 wt %, 1 to 7 wt %, 1 to 6 wt %, 1 to 5 wt %, 1 to 4 wt %, 1 to 3 wt %, or 1 to 2 wt % of the gel. The at least one polymer can be about 30 wt %, 25 wt %, 20 wt %, 15 wt %, 14 wt %, 13 wt %, 12 wt %, 11 wt %, 10 wt %, 9 wt %, 8 wt %, 7 wt %, 6 wt %, 5 wt %, 4 wt %, 3 wt %, 2 wt %, 1 wt % of the gel, or any range or sub-range between any of these values.

In various embodiments, the at least one adsorbent is chosen from porous silica, zinc ricinoleate, polyacrylamide, activated carbon, a molecular sieve, and mixtures thereof. The molecular sieve can be a zeolite or a metal organic framework material. Suitable zeolites can include zeolites having a Natrolite framework (NAT), Edingtonite framework (EDI), Thomsonite framework (THO), Analcime framework (ANA), Laumontite (LAU), Phillipsite framework (PHI), Gismondine framework (GIS), Boggsite (BOG), merlinoite (MER), mazzite-series (MAZ), paulingite-series (PAU), perlialite (Linde type L framework, zeolite L, LTL), Chabazite framework (CHA), Faujasite framework (FAU): faujasite-series, Linde type X (zeolite X, X zeolites), Linde type Y (zeolite Y, Y zeolites), Mordenite framework (MOR), Offretite-wenkite subgroup, Heulandite framework (HEU), Stilbite framework (STI), or a Brewsterite framework (BRE). In various embodiments, the adsorbent is porous silica. Porous silica can be mesoporous silica or mesoporous silica nanoparticles (MSNs).

The porous silica can have pores ranging in size from 0.5 nm to 40 nm, and can include, without limitation, porous silica materials such as MCM, SBA-15, TUD-1, HMM-33, and FSM-16. The porous silica can have pore sizes ranging from about 0.5 nm to 40 nm, 5 nm to 40 nm, 1 nm to 35 nm, 5 nm to 35 nm, 5 nm to 30 nm, 10 nm to 30 nm, 10 nm to 25 nm, 10 nm to 20 nm, 15 nm to 20 nm, or any range or sub-range between these values. The porous silica can have a pore size of 40 nm, 35 nm, 30 nm, 28 nm, 26 nm, 24, nm, 22 nm, 20 nm, 19 nm, 18 nm, 17 nm, 16 nm, 15 nm, 14 nm, 13 nm, 12 nm, 11 nm, 10 nm, 8 nm, 6 nm, 4 nm 2 nm, 1 nm, 0.5 nm, or any range or sub-range between these values. In various embodiments, the porous silica has a pore size of about 10 to about 20 nm.

The surface area of the porous silica can be from about 200 $m^2/g$ to 3000 $m^2/g$, 200 $m^2/g$ to 2800 $m^2/g$, 200 $m^2/g$ to 2600 $m^2/g$, 200 $m^2/g$ to 2400 $m^2/g$, 200 $m^2/g$ to 2200 $m^2/g$, 200 $m^2/g$ to 2000 $m^2/g$, 200 $m^2/g$ to 1800 $m^2/g$, 200 $m^2/g$ to 1600 $m^2/g$, 200 $m^2/g$ to 1400 $m^2/g$, 200 $m^2/g$ to 1200 $m^2/g$, 200 $m^2/g$ to 1000 $m^2/g$, 200 $m^2/g$ to 800 $m^2/g$, 200 $m^2/g$ to 600 $m^2/g$, 200 $m^2/g$ to 400 $m^2/g$, or any range or sub-range between these values. In various embodiments, the porous silica adsorbent has a surface area of about 3000 $m^2/g$, 2800 $m^2/g$, 2700 $m^2/g$, 2600 $m^2/g$, 2500 $m^2/g$, 2400 $m^2/g$, 2300 $m^2/g$, 2200 $m^2/g$, 2100 $m^2/g$, 2000 $m^2/g$, 1800 $m^2/g$, 1600 $m^2/g$, 3000 $m^2/g$, 1400 $m^2/g$, 1200 $m^2/g$, 1000 $m^2/g$, 800 $m^2/g$, 600 $m^2/g$, 400 $m^2/g$, 200 $m^2/g$, or any range or sub-range between these values. In various embodiments, the porous silica has a pore size of 2200 $m^2/g$.

In various embodiments, the at least one adsorbent is about 1 to about 30 wt % of the gel. The at least one adsorbent can be about 1 to 25 wt %, 1 to 20 wt %, 1 to 15 wt %, 1 to 10 wt %, 1 to 9 wt %, 1 to 8 wt %, 1 to 7 wt %, 1 to 6 wt %, 1 to 5 wt %, 1 to 4 wt %, 1 to 3 wt %, or 1 to 2 wt % of the gel. The at least one adsorbent can be about 30 wt %, 25 wt %, 20 wt %, 15 wt %, 14 wt %, 13 wt %, 12 wt %, 11 wt %, 10 wt %, 9 wt %, 8 wt %, 7 wt %, 6 wt %, 5 wt %, 4 wt %, 3 wt %, 2 wt %, 1 wt % of the gel, or any range or sub-range between any of these values.

In various embodiments, the at least one chelating agent can be chosen from sodium tripolyphosphate, sodium polyphosphate, sodium hexametaphosphate, sodium pyrophosphate, nitrilotriacetic acid, diethylene triamine pentaacetic acid, ethylene glycol-bis-(β-aminoethyl ether)-N,N-tetraacetic acid, tetrasodium pyrophosphate, and aminotrimethylene phosphonate. In various embodiments, the chelating agent is sodium hexametaphosphate.

The at least chelating agent can be about 0.01 to 20 wt % of the gel. The at least one chelating agent can be about 0.01 to 15 wt %, 0.01 to 10 wt %, 0.01 to 9 wt %, 0.01 to 8 wt %, 0.01 to 7 wt %, 0.01 to 6 wt %, 0.01 to 5 wt %, 0.01 to 4 wt %, or 0.01 to 3 wt % of the gel. The at least one chelating agent can be about 20 wt %, 15 wt %, 14 wt %, 13 wt %, 12 wt %, 11 wt %, 10 wt %, 9 wt %, 8 wt %, 7 wt %, 6 wt %, 5 wt %, 4 wt %, 3 wt %, 2 wt %, 1 wt %, 0.5 wt %, 0.25 wt %, 0.1 wt %, 0.05 wt % of the gel, or any range or sub-range between any of these values. In various embodiments, the at least chelating agent is present in an amount of 0.1 to 5 wt % of the gel.

The air pollutant can include at least one volatile organic compound (VOC), such as formaldehyde, benzene, toluene, xylene, para-dichlorobenzene, ethyl benzene, styrene, acetaldehyde, cyclohexanone, isophorone, methanol, ethanol, phenol, acetone, ethyl acetate, n-butanol methyl isobutyl ketone, n-butyl acetate, acetophenone, methyl ethyl ketone, isopropyl alcohol, dichloromethane, trichloroethylene, n-hexane, 2-methoxyethyl acetate, nitrobenzene, bis-(2-methoxyethyl)ether, 1,3,5-trimethylbenzene, and mixtures thereof. In various embodiments, the VOC is formaldehyde.

In various embodiments, the at least one component reactive with at least one air pollutant is chosen from 2-(diethanolamino) ethanesulfonic acid, aminoethanesulfonic acid, trimethylolmethylaminoethanesulfonic acid. N-(2-acetylamino)-2-aminoethanesulfonate, adipic acid dihydrazide, propionyl hydrazide, trimethylolaminomethane, ammonium sulfate, diethylenetriamine, triethylenetetramine, methyl acetoacetate, dimethyl malonate esters, and mixtures thereof. In various embodiments, the at least one component reactive with at least one air pollutant is aminoethanesulfonic acid.

The at least one component reactive with at least one air pollutant can be about 0.01 to 20 wt % of the gel. The at least one component reactive with at least one air pollutant can be about 0.01 to 15 wt %, 0.01 to 10 wt %, 0.01 to 9 wt %, 0.01 to 8 wt %, 0.01 to 7 wt %, 0.01 to 6 wt %, 0.01 to 5 wt %, 0.01 to 4 wt %, or 0.01 to 3 wt % of the gel. The at least one component reactive with at least one air pollutant can be about 20 wt %, 15 wt %, 14 wt %, 13 wt %, 12 wt %, 11 wt %, 10 wt %, 9 wt %, 8 wt %, 7 wt %, 6 wt %, 5 wt %, 4 wt %, 3 wt %, 2 wt %, 1 wt %, 0.5 wt %, 0.25 wt %, 0.1 wt %, 0.05 wt % of the gel, or any range or sub-range between any of these values. In various embodiments, the at least one component reactive with at least one air pollutant is present in an amount of 0.1 to 5 wt % of the gel.

In various embodiments, the gel can further include a crosslinking agent. The crosslinking can be chosen from sodium chloride, magnesium chloride, potassium chloride, barium chloride, magnesium sulfate, sodium sulfate, potassium sulfate, potassium hydrogen sulfate, sodium carbonate, potassium carbonate, potassium hydrogen carbonate, sodium bicarbonate, magnesium carbonate, and mixtures thereof. The crosslinking agent can give the hydrogel more rigidity when incorporated in the hydrogel matrix. In various embodiments, the crosslinking agent is potassium chloride.

The crosslinking agent can be about 0.01 to 20 wt % of the gel. The crosslinking agent can be about 0.01 to 15 wt %, 0.01 to 10 wt %, 0.01 to 9 wt %, 0.01 to 8 wt %, 0.01 to 7 wt %, 0.01 to 6 wt %, 0.01 to 5 wt %, 0.01 to 4 wt %, or 0.01 to 3 wt % of the gel. The crosslinking agent can be about 20 wt %, 15 wt %, 14 wt %, 13 wt %, 12 wt %, 11 wt %, 10 wt %, 9 wt %, 8 wt %, 7 wt %, 6 wt %, 5 wt %, 4 wt %, 3 wt %, 2 wt %, 1 wt %, 0.5 wt %, 0.25 wt %, 0.1 wt %, 0.05 wt % of the gel, or any range or sub-range between any of these values. In various embodiments, crosslinking agent is present in an amount of 0.1 to 5 wt % of the gel.

In various embodiments, an apparatus for removing one or more air pollutants from air, includes at least one fan unit, a chamber containing activated carbon or a gel that removes one or more air pollutants, wherein the gel includes about 1 to 10 wt % of carrageenan, about 1 to about 10 wt % of porous silica, about 0.1 to about 5 wt % of potassium chloride, about 0.1 to about 5 wt % of sodium hexametaphosphate, about 0.1 to about 5 wt % of aminoethanesulfonic acid, and water. In various embodiments, a method of removing air pollutants from air, includes passing air containing air pollutants through the apparatus of claim 1.

EXAMPLES

Various embodiments of the present invention can be better understood by reference to the following Examples which are offered by way of illustration. The present invention is not limited to the Examples given herein.

Example 1. Gel Composition

Carrageenan (50 g, 5 wt %, wherein wt %'s in this Example designate total wt % of the final mixture, CAS NO: 9000-07-1 from Sigma-Aldrich) was added to ion-exchanged water (840 mL, 84 wt %), mixed well, then heated to 40-95° C. with stirring to form a mixture. Porous silica (50 g, 5 wt %, average pore size 10-20 nm, 2200 m$^2$/g surface area, Sigma-Aldrich), potassium chloride (10 g, 1 wt %, Sigma-Aldrich), sodium hexametaphosphate (20 g, 2 wt %, Evonik Industries AG) and aminoethanesulfonic acid (30 g, 3 wt %, Sigma-Aldrich) were then added to the mixture, and stirred for 10-30 min to form a final mixture. The final mixture was then rapidly transferred to a target container to form the gel.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Enumerated Embodiments

The following exemplary embodiments are provided, the numbering of which is not to be construed as designating levels of importance:

Embodiment 1 provides an apparatus for removing one or more air pollutants from air, comprising: at least one fan unit; and a chamber containing either activated carbon or a gel that removes one or more air pollutants.

Embodiment 2 provides the apparatus of embodiment 1, wherein the air pollutants comprise at least one volatile organic compound (VOC).

Embodiment 3 provides the apparatus of any one of embodiments 1-2, wherein the VOC comprises formaldehyde, benzene, toluene, xylene, para-dichlorobenzene, ethyl benzene, styrene, acetaldehyde, cyclohexanone, isophorone, methanol, ethanol phenol, acetone, ethyl acetate, n-butanol, methyl isobutyl ketone, n-butyl acetate, acetophenone, methyl ethyl ketone, isopropyl alcohol, dichloromethane, trichloroethylene, n-hexane, 2-methoxylethyl acetate, nitrobenzene, bis-(2-methyoxyethyl)ether, 1,3,5-trimethylbenzene, and mixtures thereof.

Embodiment 4 provides the apparatus of any one of embodiments 1-3, wherein the VOC is formaldehyde.

Embodiment 5 provides the apparatus of any one of embodiments 1-4, wherein the fan unit comprises a battery.

Embodiment 6 provides the apparatus of any one of embodiments 1-5, wherein the fan unit comprises an air inlet.

Embodiment 7 provides the apparatus of any one of embodiments 1-6, wherein the air inlet channels air into the chamber.

Embodiment 8 provides the apparatus of any one of embodiments 1-7 further comprising an air outlet.

Embodiment 9 provides the apparatus of any one of embodiments 1-8, wherein air passes from the chamber into the air outlet and out into the surrounding air.

Embodiment 10 provides the apparatus of any one of embodiments 1-9, wherein the chamber comprises a removable cartridge comprising either the activated carbon or the gel for removing air pollutants.

Embodiment 11 provides the apparatus of any one of embodiments 1-10, wherein the gel comprises: at least one polymer; at least one adsorbent; at least one chelating agent; at least one component reactive with at least one air pollutant; and water.

Embodiment 12 provides the apparatus of any one of embodiments 1-11, wherein the concentration of one or more air pollutants exiting the air outlet is at least two times lower than the concentration of air pollutants entering the air inlet.

Embodiment 13 provides the apparatus of any one of embodiments 1-12, wherein the activated carbon is present in about 5 to about 90 wt % of the apparatus.

Embodiment 14 provides the apparatus of any one of embodiments 1-13, wherein the gel is present in about 5 to about 90 wt % of the apparatus.

Embodiment 15 provides the apparatus of any one of embodiments 1-14, wherein the at least one polymer is chosen from acacia, gelatin, carrageenan, locust bean gum, konjac gum, xanthan gum, starch, cyclodextrin, sodium alginate, chitosan, carboxymethyl chitosan, polyvinyl alcohol, polyuria, and mixtures thereof.

Embodiment 16 provides the apparatus of any one of embodiments 1-15, wherein the at least one adsorbent is chosen from porous silica, zinc ricinoleate, polyacrylamide, activated carbon, molecular sieve, and mixtures thereof.

Embodiment 17 provides the apparatus of any one of embodiments 1-16, wherein the at least one chelating agent is chosen from sodium tripolyphosphate, sodium polyphosphate, sodium hexametaphosphate, sodium pyrophosphate, nitrilotriacetic acid, diethylene triamine pentaacetic acid, ethylene glycol bis-(β-aminoethyl ether)-N,N-tetraacetic acid, tetrasodium pyrophosphate, and aminotrimethylene phosphonate.

Embodiment 18 provides the apparatus of any one of embodiments 1-17, wherein the at least one component reactive with at least one air pollutant is chosen from 2-(diethanolamino) ethanesulfonic acid, aminoethanesulfonic acid, trimethylolmethylaminoethanesulfonic acid. N-(2-acetylamino)-2-aminoethanesulfonate, adipic acid dihydrazide, propionyl hydrazide, trimethylolaminomethane, ammonium sulfate, diethylenetriamine, triethylenetetramine, methyl acetoacetate, dimethyl malonate esters, and mixtures thereof.

Embodiment 19 provides the apparatus of any one of embodiments 1-18, wherein the gel further comprises a crosslinking is chosen from sodium chloride, magnesium chloride, potassium chloride, barium chloride, magnesium sulfate, sodium sulfate, potassium sulfate, potassium hydrogen sulfate, sodium carbonate, potassium carbonate, potassium hydrogen carbonate, sodium bicarbonate, magnesium carbonate, and mixtures thereof.

Embodiment 20 provides an apparatus for removing one or more air pollutants from air, comprising: at least one fan unit; and a chamber containing activated carbon or a gel that removes one or more air pollutants, wherein the gel comprises: about 1 to about 10 wt % of crageenan; about 1 to about 10 wt % of porous silica; about 0.1 to about 5 wt % of potassium chloride; about 0.1 to about 5 wt % of sodium hexametaphosphate; about 0.1 to about 5 wt % of aminoethanesulfonic acid; and water.

Embodiment 21 provides a method of removing air pollutants from air, comprising: passing air containing air pollutants through the apparatus of any one of embodiments 1-20.

What is claimed is:

1. An apparatus for removing one or more air pollutants from air, comprising:
at least one fan unit; and
a chamber containing alternating layers of an activated carbon and a gel wherein the alternating layers of the activated carbon and the gel together remove the one or more air pollutants.

2. The apparatus of claim 1, wherein the one or more air pollutants comprise at least one volatile organic compound (VOC).

3. The apparatus of claim 2, wherein the at least VOC comprises formaldehyde, benzene, toluene, xylene, para-dichlorobenzene, ethyl benzene, styrene, acetaldehyde, cyclohexanone, isophorone, methanol, ethanol, phenol, acetone, ethyl acetate, n-butanol, methyl isobutyl ketone, n-butyl acetate, acetophenone, methyl ethyl ketone, isopropyl alcohol, dichloromethane, trichloroethylene, n-hexane, 2-methoxyethyl acetate, nitrobenzene, his-(2-methyoxyethyl)ether, 1,3,5-trimethylbenzene, and mixtures thereof.

4. The apparatus of claim 2, wherein the at least one VOC is formaldehyde.

5. The apparatus of claim 1, wherein the at least one fan unit comprises a battery.

6. The apparatus of claim 1, wherein the at east one fan unit comprises an air inlet.

7. The apparatus of claim 6, further comprising an air outlet.

8. The apparatus of claim 7, wherein air passes from the chamber into the air outlet and out into surrounding air.

9. The apparatus of claim 8, wherein the concentration of the one or more air pollutants exiting the air outlet is at least two times lower than the concentration of the one or more air pollutants entering the air inlet.

10. The apparatus of claim 1, wherein the chamber comprises a removable cartridge comprising the alternating layers of the activated carbon and the gel for removing air pollutants.

11. The apparatus of claim 1, wherein the gel comprises:
at least one polymer;
at least one adsorbent;
at least one chelating agent;
at least one component reactive with at least one air pollutant; and
water.

12. The apparatus of claim 11, wherein the at least one polymer is chosen from acacia, gelatin, carrageenan, locust bean gum, konjac gum, xanthan gum, starch, cyclodextrin, sodium alginate, chitosan, carboxymethyl chitosan, polyvinyl alcohol, polyuria, and mixtures thereof.

13. The apparatus of claim 11, wherein the at least one adsorbent is chosen from porous silica, zinc ricinoleate, polyacrylamide, activated carbon, molecular sieve, and mixtures thereof.

14. The apparatus of claim 11, wherein the at least one chelating agent is chosen from sodium tripolyphosphate, sodium polyphosphate, sodium hexametaphosphate, sodium pyrophosphate, nitrilotriacetic acid, diethylene triamine pentaacetic acid, ethylene glycol bis-(β-aminoethyl ether)-N,N-tetraacetic acid, tetrasodium pyrophosphate, and aminotrimethylene phosphonate.

15. The apparatus of claim 11, wherein the at least one component reactive with at least one air pollutant is chosen from 2-(diethanolamino) ethanesulfonic acid, aminoethanesulfonic acid, trimethylolmethylaminoethanesulfonic acid, N-(2-acetylamino)-2-aminoethanesulfonate, adipic acid dihydrazide, propionyl hydrazide, trimethylolaminomethane, ammonium sulfate, diethylenetriamine, triethylenetetramine, methyl acetoacetate, dimethyl malonate esters, and mixtures thereof.

16. The apparatus of claim 11, wherein the gel further comprises a crosslinking agent that is chosen from sodium chloride, magnesium chloride, potassium chloride, barium chloride, magnesium sulfate, sodium sulfate, potassium sulfate, potassium hydrogen sulfate, sodium carbonate, potassium carbonate, potassium hydrogen carbonate, sodium bicarbonate, magnesium carbonate, and mixtures thereof.

17. The apparatus of claim 1, wherein the activated carbon is present in about 5 to about 90 wt % of the apparatus.

18. The apparatus of claim 1, wherein the gel is present in about 5 to about 90 wt % of the apparatus.

19. A method of removing air pollutants from air, comprising:
  passing air containing air pollutants through the apparatus of claim 1.

20. An apparatus for removing one or more air pollutants from air, comprising:
  at least one fan unit; and
  a chamber containing alternating layers of an activated carbon and a gel that together removes the one or more air pollutants, wherein the gel comprises:
    about 1 to about 10 wt % of carrageenan;
    about 1 to about 10 wt % of porous silica;
    about 0.1 to about 5 wt % of potassium chloride;
    about 0.1 to about 5 wt % of sodium hexametaphosphate;
    about 0.1 to about 5 wt % of aminoethanesulfonic acid; and
    water.

* * * * *